United States Patent [19]

Sach

[11] Patent Number: 4,537,891
[45] Date of Patent: Aug. 27, 1985

[54] 2-(3,5-SUBSTITUTED-2-PYRIDYLALK-YLAMINO)-5-BENZYL-4-PYRIMIDONES

[75] Inventor: George S. Sach, Welwyn, England

[73] Assignee: Smith Kline & French Laboratories Limited, Welwyn Garden City, England

[21] Appl. No.: 537,457

[22] Filed: Sep. 29, 1983

[30] Foreign Application Priority Data

Oct. 1, 1982 [GB] United Kingdom ............... 8228029
Dec. 2, 1982 [GB] United Kingdom ............... 8234381
Jul. 23, 1983 [GB] United Kingdom ............... 8319875

[51] Int. Cl.³ ............... A61K 31/505; C07D 239/02
[52] U.S. Cl. ............... 514/272; 544/320
[58] Field of Search ............... 544/320; 424/251

[56] References Cited

U.S. PATENT DOCUMENTS 4,145,546  3/1979  Brown et al. ............... 544/310
4,154,834  5/1979  Brown et al. ............... 544/310
4,385,058  5/1983  Cooper et al. ............... 544/320
4,444,772  4/1984  Sach ............... 424/251
4,486,434  12/1984  Sach ............... 424/251

FOREIGN PATENT DOCUMENTS 68833  1/1983  European Pat. Off. .

OTHER PUBLICATIONS

Derwent Abstract 5126k, eq. EP68833.
Alfred Burger, Medicinal Chem. 3rd edition, p. 71.

Primary Examiner—Donald G. Daus
Assistant Examiner—Cecilia Shen
Attorney, Agent, or Firm—Joan S. Keps; Richard D. Foggio; Alan D. Lourie

[57] ABSTRACT 3,5-Disubstituted-2-pyridylalkylamino-5-optionally substituted benzyl-4-pyrimidones having histamine $H_1$-antagonist activity are disclosed.

17 Claims, No Drawings

2-(3,5-SUBSTITUTED-2-PYRIDYLALKYLAMINO)-5-BENZYL-4-PYRIMIDONES

This invention relates to certain pyrimidone derivatives, a process for their preparation, compositions containing them and their use as histamine $H_1$-antagonists.

Histamine, a physiologically active compound endogenous in mammals, exerts its action by interacting with certain sites called receptors. One type of receptor is known as a histamine $H_1$-receptor (Ash and Schild, Brit. J. Pharmac. 1966, 27, 427) and the actions of histamine at these receptors are inhibited by drugs commonly called "antihistamines" (histamine $H_1$-antagonists) a common example of which is mepyramine. A second type of histamine receptor is known as the $H_2$-receptor (Black et al Nature 1972, 236, 385). The actions of histamine at these receptors are not inhibited by mepyramine but are inhibited by burimamide. Compounds which inhibit the actions of histamine at histamine $H_2$-receptors are called histamine $H_2$-antagonists.

U.S. Pat. No. 4,145,546 discloses compounds of general formula (1):

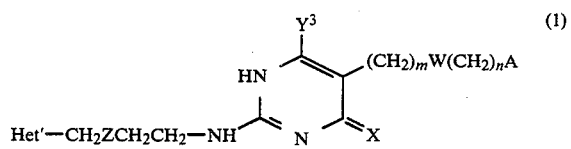

and pharmaceutically acceptable salts thereof where inter alia Het' can be a 2-pyridyl group optionally substituted by lower alkyl, lower alkoxy, halogen, amino or hydroxy or a 2-pyridyl group which is disubstituted by lower alkoxy groups, Z can be a methylene group; X can be oxygen; $-(CH_2)_mW(CH_2)_n-$ can be $-CH_2-$; A can be a 1,3-benzodioxolyl group, a phenyl group substituted with one or more lower alkyl, lower alkoxy, halogen, arylalkoxy, hydroxy, lower alkoxy-lower alkoxy, trifluoromethyl, di(lower alkyl)amino, phenoxy, halophenoxy, alkoxyphenoxy, phenyl, halophenyl or alkoxyphenyl groups and $Y^3$ is hydrogen or lower alkyl. These compounds are described as having combined histamine $H_1$- and $H_2$-antagonist activity.

A group of compounds has now been discovered in which the relative level of $H_1$ to $H_2$ activity is increased. These compounds are useful as histamine $H_1$-antagonists, that is, for the treatment of diseases for example bronchial asthma, rhinitis, hayfever and allergic eczema whose symptoms are mediated through the action of histamine at $H_1$-receptors.

Accordingly the present invention provides compounds of formula (2):

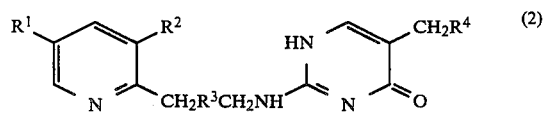

and pharmaceutically acceptable salts thereof; where $R^1$ is halogen, nitro, amino (or a pharmaceutically acceptable derivative of the amino group which is convertible in vivo into amino) or $C_{1-4}$ alkyl;

$R^2$ is halogen, nitro, amino (or a pharmaceutically acceptable derivative of the amino group which is convertible in vivo into amino), $C_{1-4}$ alkyl or $C_{3-4}$ alkoxy;

$R^3$ is a $C_{1-3}$ alkylene group; and $R^4$ is phenyl optionally bearing one or two substituents which are the same or different and are halogen, hydroxy, $C_{1-4}$ alkyl or $C_{1-4}$ alkoxy or a methylenedioxy group.

$R^1$ and $R^2$ can represent amino or a pharmaceutically acceptable derivative thereof which is convertible in vivo into amino, that is derivatives which in vivo are hydrolysed or metabolised to a free amino group. Examples include $C_{1-4}$ alkylamino for example methylamino and $C_{1-4}$ alkanoylamino for example acetamido.

$R^1$ and $R^2$ can represent any one of the halogens, fluorine, chlorine, bromine or iodine.

Preferably $R^1$ is halogen, particularly bromine.

Examples of $C_{1-4}$ alkyl groups for $R^1$ and $R^2$ are methyl, ethyl, n-propyl, iso-propyl, n-butyl and t-butyl.

Preferably $R^2$ is either $C_{1-4}$ alkyl, particularly methyl, or amino.

Examples of $C_{3-4}$ alkoxy groups for $R^2$ are n-propoxy and n-butoxy.

By way of example $R^3$ can be methylene, 1,2-ethanediyl, or 1,3-propanediyl.

The phenyl group $R^4$ can be unsubstituted but when it is substituted, preferably the substituent is in the meta and/or para position relative to its point of attachment to the $CH_2$ group. Thus particular groups which $R^4$ represents are phenyl, 3-methoxyphenyl, 4-chlorophenyl, 4-fluorophenyl, 4-hydroxyphenyl, 4-methoxyphenyl or 5-(1,3-benzodioxolyl).

Examples of compounds within the scope of this invention are:

2-[4-(5-bromo-3-methylpyrid-2-yl)butylamino]-5-benzyl-4-pyrimidone;

2-[4-(5-bromo-3-methylpyrid-2-yl)butylamino]-5-(3-methoxybenzyl)-4-pyrimidone;

2-[4-(5-bromo-3-methylpyrid-2-yl)butylamino]-5-(4-chlorobenzyl)-4-pyrimidone;

2-[4-(5-bromo-3-methylpyrid-2-yl)butylamino]-5-(4-fluorobenzyl)-4-pyrimidone;

2-[4-(5-bromo-3-methylpyrid-2-yl)butylamino]-5-(4-hydroxybenzyl)-4-pyrimidone;

2-[4-(5-bromo-3-methylpyrid-2-yl)butylamino]-5-(4-methoxybenzyl)-4-pyrimidone;

2-[4-(5-bromo-3-methylpyrid-2-yl)butylamino]-5-[5-(1,3-benzodioxolyl)methyl]-4-pyrimidone 2-[4-(5-bromo-3-aminopyrid-2-yl)butylamino]-5-(4-fluorobenzyl)-4-pyrimidone and their pharmaceutically acceptable salts.

The compounds of formula (2) are shown and described as 4-pyrimidones which exist in equilibrium with the corresponding 6-one tautomers. These compounds also exist to a lesser extent as the hydroxy tautomers, and the pyrimidine ring may also exist in the following tautomeric forms:

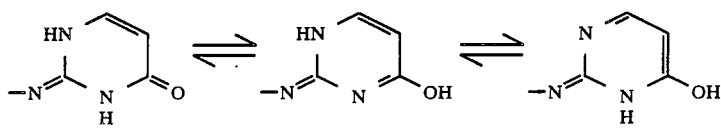

It will be understood that all these tautomeric forms are within the scope of the present invention.

The compounds of formula (2) form pharmaceutically acceptable salts with pharmaceutically acceptable salt-forming acids. Examples of these acids are hydrochloric, sulphuric, hydrobromic, phosphoric, tartaric, citric, maleic, lactic, 2-hydroxyethanesulphonic, methanesulphonic, toluene-4-sulphonic, ethanedisulphonic, ethanesulphonic and camphorsulphonic acids.

The compounds of this invention can be made by a process which comprises reacting a compound of formula (3):

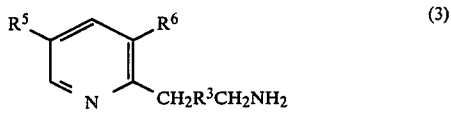

or a salt thereof, where $R^3$ is as defined with reference to formula (2), $R^5$ is a group $R^1$ or a protected amino group and $R^6$ is a group $R^2$ or a protected amino group with a compound of formula (4):

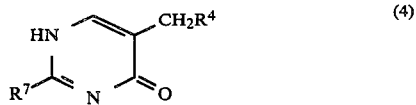

where $R^4$ is as defined with reference to formula (2) and $R^7$ is a group displaceable with amine, where necessary removing any protecting group from a protected amino group in the product so obtained, optionally converting any amino group in the product so obtained into a pharmaceutically acceptable derivative which is convertible in vivo into amino and optionally converting the compound of formula (2) so obtained into a pharmaceutically acceptable salt.

In the protected amino group $R^5$ or $R^6$ the protecting group can be any standard amino protecting group which is stable under the reaction conditions. For example it can be $C_{1-4}$ alkanoyl, benzyl or benzoyl.

These protecting groups can be introduced and removed by standard methods.

Where the protecting group is one which is either not pharmaceutically acceptable or not convertible in vivo into amino then it is removed. When the protecting group is convertible in vivo into amino then it need not be removed unless the free amino compound is required.

A free amino group can be converted by standard method into a pharmaceutically acceptable derivative which is convertible in vivo into amino. The method depends on the nature of the derivative. For example, the amino group can be alkylated or acylated.

Pharmaceutically acceptable salts of compounds of formula (2) can be prepared by standard methods, for example by reacting a solution of the compound of formula (2) with a solution of the acid.

Examples of groups $R^7$ are $C_{1-4}$ alkylthio (particularly methylthio), benzylthio, chlorine, bromine and nitroamino. Preferably $R^7$ is nitroamino.

The reaction can be carried out at an elevated temperature in the absence of a solvent, for example at from 80° to 170° C., preferably from 120° to 140° C., or in a solvent at an elevated temperature, for example at the reflux temperature of the reaction mixture. The choice of solvent is affected by solubility characteristics of the reactants and the nature of $R^7$. Preferably the solvent is pyridine, a picoline or mixture of picolines, a $C_{1-4}$ alkanol, preferably ethanol or 1-propanol, 1,2-ethanediol, a ketone, for example acetone or 2-butanone, a high boiling alkoxyaryl ether for example anisole, or a polar aprotic solvent, for example dimethylformamide, dimethylacetamide, dimethylsulphoxide, hexamethylphosphoramide, sulpholane, acetonitrile or nitromethane.

Compounds of formula (2) where $R^4$ is phenyl substituted with a hydroxy group and their salts can also be prepared by a process which comprises reacting a compound of formula (2) as previously defined where $R^4$ is phenyl substituted with a methoxy group with boron tribromide and optionally converting the product so obtained into an acid addition salt.

Compounds of formula (3) can be prepared as described or by analogy with methods described in European Patent Application Nos. 0068833 and 0068834.

Compounds of formula (3) where one of $R^5$ and $R^6$ is amino and neither $R^5$ nor $R^6$ is nitro can also be prepared as follows.

A compound of formula (5) or (6):

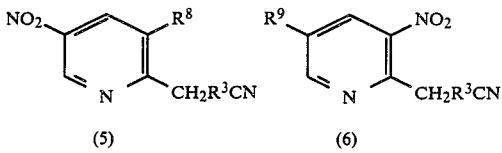

where $R^8$ is halogen, $C_{1-4}$ alkyl or $C_{3-4}$ alkoxy and $R^9$ is halogen or $C_{1-4}$ alkyl, is reacted with hydrazine and a transition metal catalyst to produce a compound of formula (7) and (8):

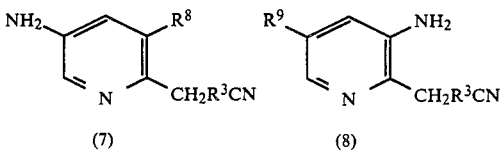

where $R^3$, $R^8$ and $R^9$ are as defined with reference to formula (5) and (6) and thereafter reacting the compound of formula (7) or (8) so obtained with more hydrazine and Raney nickel.

This reaction is carried out at a moderate temperature, for example from 5° C. to about 70° C. and preferably from about 10° C. to room temperature.

The first hydrazine reduction to prepare compounds of formula (7) and (8) can be carried out using milder hydrogenation catalysts than Raney nickel.

An example of a mild catalyst for this step is palladium on an inert support (in particular palladium on charcoal). The temperature at which the reaction is carried out depends on the catalyst. Where a mild catalyst is employed, higher temperatures for example from 55°–70° C. may be employed. With a more powerful catalyst, for example Raney nickel, the temperature does not in practice exceed 55° C.

Preferably the reaction is carried out at from 5° C. to room temperature regardless of the catalyst.

After the first step has been carried out, the compound of formula (7) or (8) can be recovered by removing the catalyst (e.g. by filtration) and evaporating the solvent. The second step can then be carried out by redissolving the compound of formula (7) or (8) so obtained in the same or a different solvent and reacting with Raney nickel and more hydrazine.

Preferably the reaction is carried out as a concerted process, that is by reacting the compound of formula (5) or (6) with sufficient hydrazine and a catalyst to form a compound of formula (7) or (8) in situ, where the catalyst for the first step is not Raney nickel, removing the catalyst (e.g. by filtration) and then adding Raney nickel and sufficient hydrazine to convert the compound of formula (7) or (8) into the corresponding compound of formula (3).

The reaction of the first or second step can be carried out in the presence of a solvent the choice of which is not critical to the success of the reaction provided that it is substantially inert to the reagents and product. Examples of solvents for use in this process include $C_{1-6}$ alkanols in particular methanol and ethanol.

The time for which the reaction in each step is allowed to proceed depends upon the nature of reagents, the temperature at which it is carried out and in the first step, the catalyst. The progress of the reaction can be monitored by standard techniques for example thin layer chromatography, and when the reaction has finished, the product can be isolated by standard techniques, for example removing the catalyst by filtration and evaporating the solvent.

The compounds of formula (4):

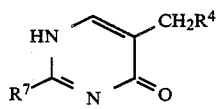

are known or can be made by analogy with known processes as disclosed in for example U.S. Pat. No. 4,145,546.

Compounds of formula (2) can also be prepared by reacting a guanidine of formula (9):

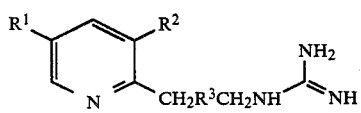

where $R^1$, $R^2$ and $R^3$ are as defined with reference to formula (2) with a compound of formula (10):

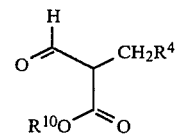

where $R^4$ is as defined with reference to formula (2) and $R^{10}$ is $C_{1-4}$ alkyl (particularly ethyl) benzyl or phenyl.

The reaction can be carried out by heating the guanidine of formula (9) with the compound of formula (10) optionally in a solvent for example an alcohol corresponding to the ester function in the compound of formula (10) that is $R^{10}OH$, at an elevated temperature, preferably in the presence of a base in particular the sodium alkoxide $NaOR^{10}$ corresponding to the ester function of the compound of formula (10).

The guanidines of formula (9) can be prepared by reacting an amine of formula (3) with a compound of formula (11):

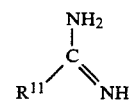

where $R^{11}$ is a leaving group for example methylthio.

The histamine $H_1$-antagonist activity of the compounds of formula (2) can be demonstrated in vitro in the guinea pig ileum test. In this test an isolated portion of the guinea pig ileum is secured under tension (500 mg) between an anchorage and a transducer in a 10 ml tissue bath and immersed in magnesium free Tyrode solution with constant aeration at a temperature of 30° C. The output from the transducer is amplified. The amplified output is in turn fed to a flat bed recorder. Measured amounts of histamine are added to the tissue bath so that the histamine concentration increases step-wise until the force of the contraction reaches a maximum. The tissue bath is washed out and filled with fresh magnesium free Tyrode solution containing compound under test. The solution is left in contact with the tissue for 8 min. and measured amounts of histamine are added again until a maximum contraction is recorded. The assay is repeated with increasing concentrations of test compound and the dose of histamine giving 50% of maximum contraction is noted. A dose ratio (DR) was calculated by comparing the concentrations of histamine required to produce 50% maximum response in the absence and in the presence of the antagonist. A plot of Log DR-1 against Log D (the concentration of compound under test) is made and the point of intersection with the Log (DR-1) ordinate is taken as the measure of the activity ($pA_2$ value). The compounds of Examples 1 to 7 have $pA_2$ values greater than 8.

The histamine $H_2$-antagonist activity of the compounds of formula (1) can be demonstrated in vitro in the guinea pig atrium test. In this test a spontaneously beating isolated portion of the guinea pig right atrium is secured under tension (300 mg) between an anchorage and a transducer in a 15 ml tissue bath and immersed in McEwens solution with constant aeration at a temperature of 37° C. The output from the transducer is amplified. Output is in turn fed to a flat bed recorder. Measured amounts of histamine are added to the tissue bath so that the histamine concentration increases step-wise until the rate of beating reaches a maximum. The tissue bath is washed out and filled with fresh McEwens solution containing compound under test. The solution is left in contact with the tissue for 60 min. and measured amounts of histamine are added again until a maximum rate is recorded. The assay is repeated with increasing concentrations of test compound and the dose of histamine giving 50% of maximum rate is noted. A dose ratio (DR) was calculated by comparing the concentrations of histamine required to produce 50% maximum response in the absence and in the presence of the antagonist. A plot of Log DR-1 against Log D (the concentration of compound under test) is made and the point of intersection with the Log (DR-1) ordinate is taken as the measure of the activity ($pA_2$ value). The compounds of Examples 1 to 7 have $pA_2$ values of less than 5.

The activity of compounds of formula (2) as histamine $H_1$-antagonists can be demonstrated in vivo by the inhibition of histamine induced bronchoconstriction. Guinea pigs of either sex are anaesthetised by intraperitoneal injection of sodium pentobarbitone, 90 mg/kg. The trachea is cannulated. The animal is respired artificially with a fixed volume of air just adequate to inflate the lungs. The pressure needed to inflate the lungs is monitored from the respiratory system using a low pressure transducer. Intravenous injection of histamine causes dose-dependent increases in the pressure to inflate the lungs reflecting the bronchoconstrictor action of histamine. Responses to histamine can be antagonised using histamine $H_1$-receptor antagonists.

Dose-response curves to histamine are established at 20, 40, 80, 160 and 320 nmols/kg. Antagonists are then administered by intravenous injection and 5 minutes later a new histamine dose-response curve is established increasing the doses of histamine as necessary. The effect of the antagonist can be quantified by the displacement, to the right, of the histamine dose-response curve, expressed as a dose-ratio. A series of doses of antagonists may be given to each animal allowing calculation of dose-ratios for each dose of antagonist.

The activity of the compounds of formula (2) as histamine $H_2$-antagonists can be demonstrated in vivo by the inhibition of histamine-stimulated secretion of gastric acid from the lumen-perfused stomachs of rats anaesthetized with urethane. This procedure is referred to in Ash and Schild, Brit. J. Pharmac. Chemother., 27, 247 (1966).

In order to use the compounds of the invention as histamine $H_1$-antagonists, they can be formulated as pharmaceutical compositions in accordance with standard pharmaceutical procedure.

The invention also includes pharmaceutical compositions comprising a compound of formula (2) or a pharmaceutically acceptable salt thereof and a pharmaceutically acceptable carrier.

Compounds of formula (2) and their pharmaceutically acceptable salts can be administered topically or systemically.

Topical formulations for administration to the skin include lotions and creams. Topical formulations for administration to the respiratory tract include solutions for application via a nebulizer or as an aerosol, or a microfine insufflatable powder. The active ingredient in an insufflatable powder has a small particle size i.e. less than 50 microns and preferably less than 10 microns. The active material is co-presented with a solid carrier for example lactose which has a particle size of less than 50 microns.

Systemic administration can be achieved by rectal, oral or parenteral administration. A typical suppository formulation comprises the active compound with a binding agent and/or including agent for example gelatine or cocoa butter or other low melting vegetable waxes or fats. Typical parenteral compositions consist of a solution or suspension of the active material in a sterile aqueous carrier of parenterally acceptable oil.

Compounds of formula (2) which are active when given orally can be formulated as syrups, tablets, capsules and lozenges. A syrup formulation generally consists of a suspension or solution of the compound in a liquid carrier for example ethanol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations can be used. Examples of such carriers include magnesium stearate, starch, lactose, glucose, sucrose, and cellulose. Preferably the composition is in unit dose form for example a tablet, capsule or metered aerosol.

Where appropriate, bronchodilators and antiasthmatics for example sympathomimetic amines particularly isoprenaline, isoetharine, salbutamol, phenylephrine and ephedrine; xanthine derivatives particularly theophylline and aminophylline; and corticosteroids particularly prednisolone and adrenal stimulants particularly ACTH can be included.

Each dosage unit for oral administration contains preferably from 1 to 200 mg of a compound of formula (2) or a pharmaceutically acceptable salt thereof calculated as the free base.

The invention also provides a method of blocking histamine $H_1$-receptors which comprises administering to a subject an effective amount to block said receptors of a compound of formula (2) or a pharmaceutically acceptable salt thereof.

The compounds of formula (2) and their pharmaceutically acceptable salts will normally be administered to a subject in a pharmaceutical composition as described above, for the treatment of rhinitis, hayfever, bronchial asthma or allergic eczema. An adult subject will receive an oral dose of between 15 mg and 400 mg and preferably between 15 mg and 200 mg or an intravenous, subcutaneous or intramuscular dose of between 1 mg and 50 mg, and preferably between 1 mg and 10 mg of a compound of formula (2) or a pharmaceutically acceptable salt thereof calculated as the free base, the composition being administered 1 to 4 times per day.

The following Examples illustrate the invention.

EXAMPLES

EXAMPLE 1

5-Bromo-2-(4-aminobutyl)-3-methylpyridine, (0.73 g), was fused with 2-methylthio-5-(4-chlorobenzyl)-4-pyrimidone (0.75 g) at 160°–170° C. and heating was continued for 6 hours. The mixture was cooled and recrystallised from chloroform/petroleum-ether (b.p. 60°–80° C.), to give 2-[4-(3-methyl-5-bromopyrid-2-yl)butylamino]-5-(4-chlorobenzyl)-4-pyrimidone (1.0 g) m.p. 149°–150° C.

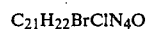

$C_{21}H_{22}BrClN_4O$

Requires C, 54.50; H, 4.79; N, 12.11; Total Halide 24.93%; Found, C, 54.30; H, 4.94; N, 12.03; Total Halide 24.79%.

EXAMPLE 2

(a) 5-(4-Methoxybenzyl)-2-thiouracil (105 g) was refluxed in glacial acetic acid (800 ml) and 48% aqueous hydrobromic acid (400 ml) for 3 hrs. The solution was cooled to ca. 35° C., methyl iodide (53 ml) was added and the solution was refluxed for a further 2 hours. The mixture was evaporated to dryness in vacuo and water (500 ml) added to the residue. Sodium hydroxide was added to raise the pH to ca. 5. The solid which formed was filtered off and recrystallised from ethanol giving 4-hydroxybenzyl-2-methylthio-4-pyrimidone (43.1 g) m.p. 243°–4° C.

(b) 5-Bromo-2-(4-aminobutyl)-3-methylpyridine, (0.875 g) and 5-(4-hydroxybenzyl)-2-methylthio-4-pyrimidone (0.745 g) were refluxed in pyridine (3 ml) for 24 hours. The pyridine was evaporated in vacuo. Residual pyridine was removed from the residue by azeotroping with water in vacuo and dried by azeotroping with ethanol. Water (20 ml) was added and the pH lowered to 6 with dilute hydrochloric acid. The solid obtained was recrystallised from ethanol/water, dimethylformamide/water and finally acetic acid/water to give 2-[4-(5-bromo-3-methylpyrid-2-yl)butylamino]-5-(4-hydroxybenzyl)-4-pyrimidone (0.54 g) m.p. 232°–4° C.

NMR (DMSO-d$_6$) assignment, δ(p.p.m.), multiplicity;

(C$\underline{H_2}$)$_2$CH$_2$NH$_2$, 1.62, m; 3-CH$_3$, 2.27, s;
C$\underline{H_2}$(CH$_2$)$_3$NH$_2$, 2.70, m; C$\underline{H_2}$NH$_2$, ca 3.2, m;
C$\underline{H_2}$(benzyl), 3.38, s; NH, ca 6.3, broad resonance;
3-H + 5-H phenyl, 6.63, m; 2-H+6-H phenyl, 6.98, m;
6-H pyrimidyl, 7.37, s; 4-H pyridyl 7.76, d; 6-H pyridyl, 8.38, d; OH, 8.96, broad s; NH, 10.5, broad resonance.

EXAMPLE 3

5-Bromo-2-(4-aminobutyl)-3-methylpyridine, (0.875 g) and 5-(4-methoxybenzyl)-2-methylthio-4-pyrimidone (0.786 g) were refluxed in pyridine (3 ml) for 20 hours. The pyridine was evaporated in vacuo. Residual pyridine was removed from the residue by azeotroping with water in vacuo and dried by azeotroping with ethanol. Addition of water (10 ml) and ethanol (1 ml) gave a colourless solid. This was recrystallised from ethanol and then from methanol to give 2-[4-(5-bromo-3-methylpyrid-2-yl)butylamino]-5-(4-methoxybenzyl)-4-pyrimidone (0.97 g) m.p. 149°–50° C.

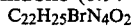

Requires C, 57.77; H, 5.51; N, 12.25; Br, 17.47; Found C, 57.85; H, 5.50; N, 12.33; Br, 17.40.

EXAMPLE 4

5-Bromo-2-(4-aminobutyl)-3-methylpyridine, (0.88 g) and 5-(4-fluorobenzyl)-2-methylthio-4-pyrimidone (0.75 g) were refluxed in pyridine (3 ml) for 24 hours. The pyridine was removed in vacuo and the residue triturated with ethanol (5 ml) giving a colourless solid. The solid was recrystallised from methanol giving 2-[4-(5-bromo-3-methylpyrid-2-yl)butylamino]-5-(4-fluorobenzyl)-4-pyrimidone (0.96 g) m.p. 172°–3° C.

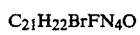

Requires C, 56.64; H, 4.98; N, 12.58; Br, 17.94; Found C, 56.64; H, 5.22; N, 12.58; Br, 17.59.

The 4-methoxybenzyl- and 4-fluorobenzyl-2-methylthio-4-pyrimidone used in Examples 3, 4 and 8 were prepared from 4-methoxybenzaldehyde and 4-fluorobenzaldehyde by the method described in U.S. Pat. No. 4,145,546.

EXAMPLE 5

5-Bromo-2-(4-aminobutyl)-3-methylpyridine, (0.58 g) and 5-(3-methoxybenzyl)-2-methylthio-4-pyrimidone (0.51 g) were refluxed in pyridine (3 ml) for 3 hours. The pyridine was removed in vacuo. The residue was recrystallised from ethanol/water giving 2-[4-(5-bromo-3-methylpyrid-2-yl)butylamino]-5-(3-methoxybenzyl)-4-pyrimidone (0.60 g). Softens 65° C., melts 73° C.

Requires C, 56.22; H, 5.66; N, 11.92; Br, 17.00; Found C, 56.17; H, 5.60; N, 12.08; Br, 17.06; Weight loss 30°–180° C.=2.7%=0.7H$_2$O.

EXAMPLE 6

5-Bromo-2-(4-aminobutyl)-3-methylpyridine, (0.88 g) and 5-(3,4-methylenedioxybenzyl)-2-methylthio-4-pyrimidone (0.83 g) were refluxed in pyridine (3 ml) for 24 hours. The pyridine was removed in vacuo and the resulting brown oil triturated with ethanol giving a cream solid which was recrystallised from dimethylformamide/ethanol giving 2-[4-(5-bromo-3-methylpyrid-2-yl)butylamino]-5-(3,4-methylenedioxybenzyl)-4-pyrimidone (1.1 g) as a colourless solid m.p. 145°–6° C.

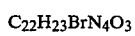

Requires C, 56.06; H, 4.92; N, 11.89; Br, 16.95; Found C, 56.17; H, 4.90; N, 12.08; Br, 16.65.

EXAMPLE 7

5-Bromo-2-(4-aminobutyl)-3-methylpyridine, (0.88 g) and 5-benzyl-2-nitroamino-4-pyrimidone (0.74 g) were refluxed in pyridine (3 ml) for 4 hours. The solvent was removed in vacuo and the residual oil partitioned between chloroform and water at pH 5. The chloroform extracts were dried over magnesium sulphate and evaporated to an oil. Recrystallisation from ethanol/ethyl acetate gave 2-[4-(5-bromo-3-methylpyrid-2-yl)butylamino]-5-benzyl-4-pyrimidone (0.65 g) m.p. 138°–9° C.

Requires C, 59.02; H, 5.42; N, 13.11; Br, 18.70; Found C, 58.81; H, 5.49; N, 13.09; Br, 18.82.

EXAMPLE 8

(a) A mixture of concentrated sulphuric acid (35 ml) and nitric acid (35 ml) was added dropwise with stirring to a chilled (5° C.) solution of 2-amino-5-bromopyridine (50.3 g) in concentrated sulphuric acid (240 ml) maintaining the temperature of the reaction mixture at 5°–6° C. throughout the addition. When the addition was complete, the reaction mixture was stirred for a further 1.0 hr. at 5°–8° C. and then warmed to 30° C. and allowed to stand for ca 18 hr.

Further concentrated nitric acid (35 ml) was added portionwise to the reaction mixture with stirring while maintaining the temperature at 30°–40° C. A portion (50 ml) of the solution was poured into hot (ca 70° C.) water (100 ml) with rapid stirring and this mixture was heated to 120° C. Gas evolved. When the evolution of gas ceased further portions (75 ml) of the reaction mixture were added maintaining the temperature at 120° C. When the additions were completed, the solution obtained was poured into ice (1 kg) and chilled in a salt/ice bath. Fine orange crystals formed which were removed by filtration and recrystallised from dimethylformamide/water to give 2-hydroxy-3-nitro-5-bromopyridine (23.5 g) m.p. 240°–243° C.

(b) A solution of 2-hydroxy-3-nitro-5-bromopyridine (23.4 g) in phosphoryl chloride (16 ml) was heated under reflux for 2.5 hr. The reaction mixture was poured into ice/water and a brown solid was produced which was removed by filtration. The solid was dissolved in chloroform, dried (MgSO₄) and decolourised by heating with charcoal for 30 min. The solvent was evaporated from the decolourised solution to yield a yellow solid (24.0 g) which was recrystallised from ether/petroleum ether (40°–60° C.) to yield 2-chloro-3-nitro-5-bromopyridine (19.4 g) m.p. 66°–68° C.

(c) A solution of 2-(2-cyanoethyl)malonic acid diethyl ester (24.2 g) in tetrahydrofuran (15 ml) was added to a suspension of sodium hydride (2.45 g) in tetrahydrofuran (30 ml) at 20° C. under nitrogen. To this was added 2-chloro-3-nitro-5-bromopyridine (22 g) and the mixture so obtained was heated to 93°–95° C. A small amount of tetrahydrofuran was allowed to distil off. The mixture was heated under reflux for 2.5 hr. The reaction mixture was poured into water and neutralised to pH 7 with concentrated hydrochloric acid. The aqueous phase was extracted with chloroform, dried (MgSO₄) decolourised with charcoal and filtered through a silica column. The chloroform eluant was evaporated to yield an oil which slowly crystallised. The crystals were washed in petroleum ether (40°–60° C.) and dried to yield 4-(5-bromo-3-nitropyrid-2-yl)-4,4-bis(carbethoxy)butyronitrile (28 g) m.p. 58°–62° C.

(d) 4-(5-Bromo-3-nitropyrid-2-yl)-4,4-bis(carbethoxy)butyronitrile (21.8 g) was added to a mixture of aqueous sodium hydroxide solution (1M, 263.6 ml) and methanol (635 ml). The mixture so obtained was stirred for 18 hr. The mixture was acidified to pH 1.5 by addition of concentrated hydrochloric acid and heated at 50° C. for 4.75 hr. The solution was neutralised to pH 7 with sodium hydroxide solution and the methanol removed by distillation. The aqueous solution remaining was extracted with chloroform to give an oil (11.2 g) which was chromatographed on a silica column with chloroform to give 5-bromo-3-nitro-2-(3-cyanopropyl)pyridine (9.6 g) as a yellow solid m.p. 73°–76° C.

(e) Raney nickel moist with ethanol (34 g) was added to a suspension of finely divided 5-bromo-3-nitro-2-(3-cyanopropyl)pyridine (8.4 g) in ethanol (350 ml) under nitrogen. The mixture was cooled (10° C.) and a solution of hydrazine hydrate (2.34 ml) in ethanol (10 ml) was added maintaining the reaction temperature between 12°–15° C. The reaction mixture was allowed to warm to room temperature with constant stirring and hydrazine hydrate (15.5 ml) was added in portions (2.3 ml) in ethanol (3 ml) at regular intervals over 46 hr. Before each addition the reaction mixture was cooled to 15° C. After 23 hr. more Raney nickel (6 g) was added. The reaction was stopped after 47 hr. The catalyst was removed by filtering the reaction mixture through a pad of diatomaceous earth. Evaporation of the solvent yielded an oil (7.9 g) which was chromatographed on a silica column eluting with ethyl acetate/ethanol/0.880 ammonia 15:10:2 to give 3-amino-5-bromo-2-(4-aminobutyl)pyridine (4.0 g) as an oil.

(f) 3-Amino-2-(4-aminobutyl)-5-bromopyridine (0.5 g) and 2-methylthio-5-(4-fluorobenzyl)-4-pyrimidone (0.51 g) were refluxed in pyridine (1.5 ml) for 20.5 hrs. The pyridine was removed in vacuo and the residue was re-evaporated with n-propanol (2×20 ml) giving a brown oil (1.12 g). The oil was chromatographed on silica in ethyl acetate/ethanol/0.880 ammonia (15:10:2). The product was crystallised from acetonitrile/water (9:1) to give 2-[4-(3-amino-5-bromopyrid-2-yl)butylamino]-5-(4-fluorobenzyl)-4-pyrimidone (0.53 g) m.p. 146°–148° C.

What is claimed is:

1. A compound of formula (2):

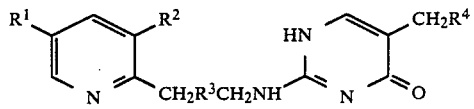

or a pharmaceutically acceptable salt thereof; where
$R^1$ is halogen, nitro, amino, $C_{1-4}$ alkylamino, $C_{1-4}$ alkanoylamino or $C_{1-4}$ alkyl;
$R^2$ is halogen, nitro, amino, $C_{1-4}$ alkylamino, $C_{1-4}$ alkanoylamino, $C_{1-4}$ alkyl or $C_{3-4}$ alkoxy; provided that $R^1$ and $R^2$ are not both selected from amino, $C_{1-4}$ alkylamino, $C_{1-4}$ alkanoylamino and nitro;
$R^3$ is a $C_{1-3}$ alkylene group; and
$R^4$ is phenyl optionally bearing one or two substituents which are the same or different and are halogen, hydroxy, $C_{1-4}$ alkyl or $C_{1-4}$ alkoxy or a methylenedioxy group.

2. A compound according to claim 1, where $R^1$ is halogen.

3. A compound according to claim 1 or claim 2, where $R^1$ is bromine.

4. A compound according to claim 1, where $R^2$ is $C_{1-4}$ alkyl.

5. A compound according to claim 4, where $R^2$ is methyl.

6. A compound according to claim 1, where $R^2$ is amino.

7. A compound according to claim 1, where $R^4$ is phenyl, 3-methoxyphenyl, 4-chlorophenyl, 4-fluorophenyl, 4-hydroxyphenyl, 4-methoxyphenyl or 5-(1,3-benzodioxolyl).

8. A compound according to claim 1 which is 2-[4-(5-bromo-3-methylpyrid-2-yl)butylamino]-5-benzyl-4-pyrimidone or a pharmaceutically acceptable salt thereof.

9. A compound according to claim 1 which is 2-[4-(5-bromo-3-methylpyrid-2-yl)butylamino]-5-(3-methoxybenzyl)-4-pyrimidone or a pharmaceutically acceptable salt thereof.

10. A compound according to claim 1 which is 2-[4-(5-bromo-3-methylpyrid-2-yl)butylamino]-5-(4-chlorobenzyl)-4-pyrimidone or a pharmaceutically acceptable salt thereof.

11. A compound according to claim 1 which is 2-[4-(5-bromo-3-methylpyrid-2-yl)butylamino]-5-(4-fluorobenzyl)-4-pyrimidone or a pharmaceutically acceptable salt thereof.

12. A compound according to claim 1 which is 2-[4-(5-bromo-3-methylpyrid-2-yl)butylamino]-5-(4-hydroxybenzyl)-4-pyrimidone or a pharmaceutically acceptable salt thereof.

13. A compound according to claim 1 which is 2-[4-(5-bromo-3-methylpyrid-2-yl)butylamino]-5-(4-methoxybenzyl)-4-pyrimidone or a pharmaceutically acceptable salt thereof.

14. A compound according to claim 1 which is 2-[4-(5-bromo-3-methylpyrid-2-yl)butylamino]-5-[5-(1,3-benzodioxolyl)methyl]-4-pyrimidone or a pharmaceutically acceptable salt thereof.

15. A compound according to claim 1 which is 2-[4-(5-bromo-3-aminopyrid-2-yl)butylamino]-5-(4-fluorobenzyl)-4-pyrimidone or a pharmaceutically acceptable salt thereof.

16. A pharmaceutical composition having histamine $H_1$-antagonist activity comprising an effective amount of a compound according to claim 1 and a pharmaceutically acceptable carrier.

17. A method of blocking histamine $H_1$-receptors which comprises administering to a subject an effective amount to block said receptors of a compound according to claim 1.

* * * * *